United States Patent
Tang et al.

(10) Patent No.: US 8,748,482 B2
(45) Date of Patent: Jun. 10, 2014

(54) LUBIPROSTONE CRYSTAL, THE USE AND THE METHOD FOR THE PREPARATION THEREOF

(75) Inventors: Zhijun Tang, Shanghai (CN); Zhonghao Zhuo, Shanghai (CN); Yunman Zheng, Shanghai (CN); Bingming He, Shanghai (CN); Huichun Yang, Shanghai (CN); Jushang Zheng, Shanghai (CN)

(73) Assignee: Shanghai Techwell Biopharmaceutical Co., Ltd, Shanghai (CN)

( * ) Notice: Subject to any disclaimer, the term of this patent is extended or adjusted under 35 U.S.C. 154(b) by 516 days.

(21) Appl. No.: 12/935,859

(22) PCT Filed: May 15, 2008

(86) PCT No.: PCT/CN2008/070971
§ 371 (c)(1),
(2), (4) Date: Sep. 30, 2010

(87) PCT Pub. No.: WO2009/121228
PCT Pub. Date: Oct. 8, 2009

(65) Prior Publication Data
US 2011/0028541 A1  Feb. 3, 2011

(30) Foreign Application Priority Data
Apr. 1, 2008  (CN) .......................... 2008 1 0035448

(51) Int. Cl.
*A61K 31/352* (2006.01)
*C07D 311/96* (2006.01)

(52) U.S. Cl.
USPC .......................................... 514/456; 549/396

(58) Field of Classification Search
USPC .......................................... 549/396; 514/456
See application file for complete search history.

(56) References Cited

U.S. PATENT DOCUMENTS

5,254,588 A * 10/1993 Ueno et al. ..................... 514/573

FOREIGN PATENT DOCUMENTS

| CN | 1379769  | 11/2002 |
| CN | 1655776  | 8/2005  |
| WO | 01/27099 | 4/2001  |
| WO | 02/20007 | 3/2002  |

OTHER PUBLICATIONS

Sucampo-Tanaka, drug insert for Lubiprostone, available at http://www.amitiza.com/resources/pi.pdf, 19 sheets supplied (2006).*
Whiting et al, Canadian Journal of Chem., vol. 49, p. 3799-3806 (1971).*
Lacy et al., "Lubiprostone: a chloride channel activator," Journal of Clinical Gastroenterology, 2007, vol. 41, No. 4, pp. 345-351.
International Search Report of PCT/CN2008/070971, dated Jan. 15, 2009.

* cited by examiner

*Primary Examiner* — Taylor Victor Oh
(74) *Attorney, Agent, or Firm* — Hamre, Schumann, Mueller & Larson, P.C.

(57) ABSTRACT

The present invention relates to a lubiprostone crystal, the method for the preparation thereof, and a pharmaceutical composition or kit comprising the same, as well as the use of said crystal in the preparation of a medicament for the treatment of gastrointestinal tract diseases, especially constipation. The X-ray powder diffraction pattern of said crystal comprises characteristic peaks measured at the following 2θ reflection angles: 14.6±0.2°, 17.0±0.2° and 19.6±0.2°. As compared to amorphous lubiprostone, the crystal of the present invention has the advantages of relative high purity, stable properties and easy-for-storage and use.

7 Claims, 3 Drawing Sheets

LUBIPROSTONE CRYSTAL, THE USE AND THE METHOD FOR THE PREPARATION THEREOF

TECHNICAL FIELD

The present invention relates to a lubiprostone crystal. Moreover, the present invention further relates to the use of the lubiprostone crystal in preparing a medicament for the treatment of gastrointestinal tract diseases, and a method for preparing said lubiprostone crystal.

TECHNICAL BACKGROUND

Lubiprostone, (−)-7-[(2R,4aR,5R,7aR)-2-difluoropentyl-2-hydroxy-6-oxo-octahydrocyclopenta[b]pyran-5-yl]heptanoic acid, is a kind of prostaglandin compounds, and usually exists in the following tautomeric forms:

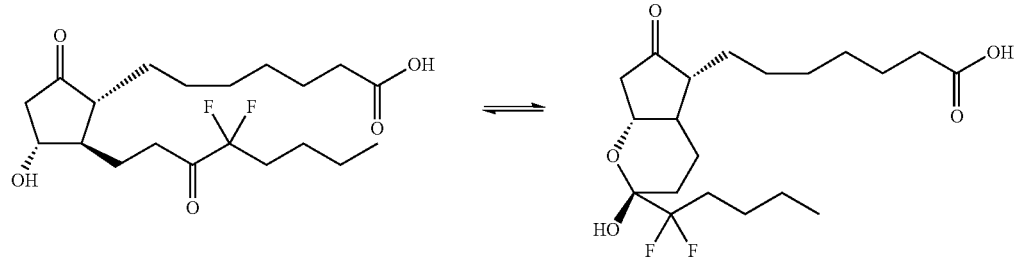

Lubiprostone, a local activator of chloride channel, can specifically activate type II chloride channel on the cell membrane of a epidermal cell in the gastrointestinal tract, stimulate the secretion of intestinal fluid having a high chloride ion concentration, and enhance the intestinal motility so as to facilitate the softened feces to move along the intestinal tract and relief the conditions of constipation. Lubiprostone capsule (lubiprostone/Amitiza, by American Sucampo Pharmaceuticals) was approved by the US Food and Drug Administration (FDA) for the treatment of chronic idiopathic constipation in adults.

However, the lubiprostone prepared and used now is in an amorphous form, which has an oily appearance. It is difficult to control the purity and homogeneity of a medicament in the procedure for the preparation of the medicament when the compound is in an amorphous form. In addition, the stability of amorphous lubiprostone is not satisfactory.

No research or report was provided for lubiprostone crystal forms in the field. Therefore, it is an urgent need for developing lubiprostone crystal suitable for the preparation of corresponding medicament.

CONTENTS OF THE INVENTION

One of the objects of the present invention is to provide a lubiprostone crystal.

A further object of the present invention is to provide a method for the preparation of said lubiprostone crystal.

Furthermore, another object of the present invention is to provide a use of said lubiprostone crystal in preparing a medicament for the treatment of gastrointestinal tract diseases.

In one aspect of the present invention, a lubiprostone crystal is provided, wherein the X-ray powder diffraction pattern of said crystal comprises characteristic peaks measured at the following 2θ reflection angles: 14.6±0.2°, 17.0±0.2° and 19.6±0.2°.

In a preferred example, the X-ray powder diffraction pattern of said crystal further comprises peaks measured at the following 2θ reflection angles: 7.6±0.2°, 8.5±0.2°, 10.6±0.2°, 17.7±0.2°, 20.1±0.2° and 23.4±0.2°.

In another preferred example, the X-ray powder diffraction pattern of said crystal further comprises peaks measured at the following 2θ reflection angles: 10.9±0.2°, 12.0±0.2°, 12.2±0.2°, 12.4±0.2°, 14.9±0.2°, 15.5±0.2°, 15.9±10.2°, 18.6±0.2°, 21.5±0.2°, 22.0±0.2°, 22.2±0.2°, 22.9±0.2°, 23.6±0.2°, 24.6±0.2°, 25.1±0.2°, 25.6±0.2°, 29.0±0.2°, 29.4±0.2°, 30.2±0.2°, 31.2±0.2°, 31.9±0.2°, 32.5±0.2°, 33.5±0.2°, 34.3±0.2°, 38.0±0.2°, 39.2±0.2°, 41.4±0.2° and 44.3±0.2°.

In another preferred example, the differential scanning calorimetry pattern of said lubiprostone crystal has a maximum absorption peak at about 61±0.2° C.

In another preferred example, the half peak width of the characteristic peaks at 2θ reflection angles in the X-ray powder diffraction pattern of the crystal is not more than 2°.

In another aspect of the present invention, a method for the preparation of said lubiprostone crystal is provided. The method comprises the following steps:

(a) dissolving lubiprostone in solvent (i) having medium or high polarity to form a lubiprostone solution; and (b) lowering the temperature and/or adding another solvent (ii) having low polarity or water to obtain said lubiprostone crystal.

In a preferred example, said solvent (i) is selected from the group consisting of: ethyl acetate, acetone, dichloromethane, tetrahydrofuran, acetonitrile, methanol, ethanol, isopropanol, and a mixture thereof.

In another preferred example, said solvent (i) is selected from the group consisting of: ethyl acetate, acetone, dichloromethane, and a mixture thereof.

In another preferred example, said solvent (ii) is selected from the group consisting of: n-hexane, n-heptane, cyclohexane, water, and a mixture thereof.

In another preferred example, said solvent (i) is n-hexane.

In another preferred example, lowering the temperature is to lower the temperature of the solution obtained in step (a) to a temperature ranging from 30° C. to −100° C.

In a preferred example, lowering the temperature is to lower the temperature of the solvent obtained in step (a) to a temperature ranging from 20° C. to −80° C., preferably from 10° C. to −50° C., and more preferably from 0° C. to −30° C.

In another aspect of the present invention, a pharmaceutical composition is provided. Said pharmaceutical composition comprises: the lubiprostone crystal of the present invention or the lubiprostone crystal prepared by the aforementioned method; and pharmaceutically acceptable carrier(s).

In a preferred example, the amount of lubiprostone crystal in the pharmaceutical composition is 0.001~99.9 wt %, preferably 1-95 wt %, more preferably 5-90 wt %, even more preferably 10~80 wt %, based on the total weight of the composition.

In another preferred example, the pharmaceutical composition further comprises other active substance(s) for treating gastrointestinal tract diseases.

In another preferred example, said other active substance(s) is a proton pump inhibitor medicament, preferably omeprazole or lansoprazole.

In another preferred example, the pharmaceutical composition is used to treat gastrointestinal tract diseases, preferably used to treat constipation.

In another aspect of the present invention, a use of the lubiprostone crystal of the present invention in the preparation of a medicament for the treatment of gastrointestinal tract diseases is provided.

In a preferred example, said pharmaceutical composition is used to stimulate the secretion of intestinal fluid having a high chloride ion concentration, to enhance the intestinal motility, to facilitate the softened feces to move along the intestinal tract, and/or to relief the symptoms of constipation.

In another aspect of the present invention, a method for the preparation of the pharmaceutical composition is provided. The method comprises the step of mixing the lubiprostone crystal with pharmaceutically acceptable carrier(s).

In another aspect of the present invention, a kit for the treatment of gastrointestinal tract diseases is provided. The kit comprises:

(i) the lubiprostone crystal of the present invention or a lubiprostone crystal prepared by the aforementioned method;

(ii) other active substance(s) for the treatment of gastrointestinal tract diseases; and (iii) an instruction.

In a preferred example, said other active substance is a proton pump inhibitor medicament, preferably omeprazole or lansoprazole.

Other aspects of the present invention are obvious to the skilled according to the contents of the context.

PARTICULAR EMBODIMENTS OF THE INVENTION

Figure 1:
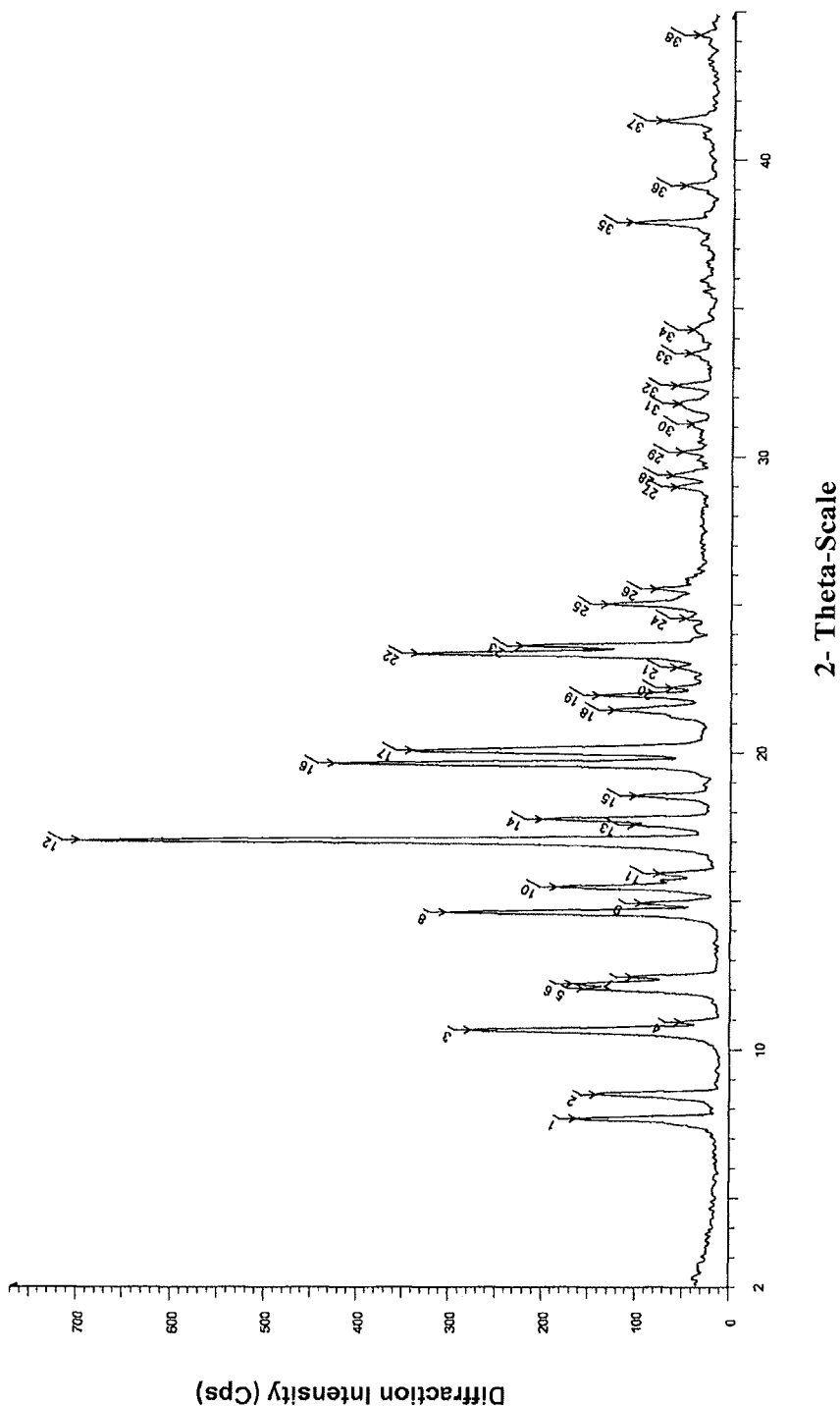
FIG. 1 is the X-ray powder diffraction (XRD) pattern of the lubiprostone crystal.

After intensive and extensive studies and experiments, the inventors of the present invention obtained the lubiprostone crystal and unexpectedly found that said crystal has excellent properties such as high purity, stable properties, and high solubility in pharmaceutical excipients (such as fat acids). The inventors have also found that the storage and use of said crystal are much more convenient than those for lubiprostone in amorphous form, and said crystal is particularly suitable for being used as the lubiprostone API (Active Pharmaceutical Ingredients) for preparing pharmaceutical compositions and kits. Based on the above researches, the present invention was completed.

Preparation of the Lubiprostone Crystal

In the present invention, the term "crystal" refers to a solid in which the complexes of atoms or molecules are arranged in a special form.

The inventors of the present invention found in the research that the lubiprostone crystal could be precipitated from the solution formed by dissolving lubiprostone in a suitable solvent after adding another solvent and/or decreasing the temperature.

In one embodiment of the present invention, two solvents are used to produce the lubiprostone crystal:

Solvent (i), which can be used to dissolve lubiprostone, is used to dissolve lubiprostone, wherein solvent (i) can be, such as, ethyl acetate, acetone, dichloromethane, methanol, ethanol, isopropanol, tetrahydrofuran, acetonitrile, or a mixture thereof; and then, Solvent (ii), which can be used to precipitate lubiprostone crystal from the solution comprising lubiprostone, was added to precipitate the lubiprostone crystal, wherein solvent (ii) can be, such as, alkane (eg. n-hexane, n-heptane, cyclohexane, and petroleum ether), water, or a mixture thereof.

In one embodiment of the present invention, the solvent which can be used to precipitate lubiprostone crystal is added in an amount ranging from 10000:1 to 0.01:1 (ml/ml) lubiprostone solution, preferably from 100:1 to 1:1 (ml/ml) lubiprostone solution. Solvent (i) is added at a temperature ranging from 0° C. to 80° C., preferably from 10° C. to 60° C., and more preferably from room temperature to 50° C. Solvent (ii) is added at a temperature ranging from −10° C. to 80° C., preferably from −5° C. to 60° C., and more preferably from 0° C. to 50° C.

In another embodiment of the present invention, the lubiprostone crystal of the present invention can be prepared by the following steps:

dissolving lubiprostone in the above mentioned solvent (i) which can be used to dissolve lubiprostone, such as, ethyl acetate, acetone, dichloromethane, methanol, ethanol, isopropanol, tetrahydrofuran, acetonitrile, or a mixture thereof; and then, lowering the temperature of the solution to precipitate the lubiprostone crystal. In one embodiment of the present invention, the temperature of the lubiprostone solution is lowered to a temperature range from 30° C. to −100° C., preferably from 20° C. to −80° C. or from 10° C. to −50° C., and more preferably from 0° C. to −30° C.

The lubiprostone crystal can also be prepared by adding solvent (ii) and simultaneously lowering the temperature of the solution after producing the solution of lubiprostone in solvent (i). In one embodiment of the present invention, solvent (ii) having low polarity is added, and the temperature of the lubiprostone solution is simultaneously lowered to a temperature ranging from 30° C. to −100° C., preferably from 10° C. to −50° C., and more preferably from 0° C. to −30° C.

The Identification and Properties of the Lubiprostone Crystal

After obtaining the lubiprostone crystal, the inventors of the present invention made further researches on the properties of said lubiprostone crystal by various methods and equipments.

"X-ray powder diffraction", also known as "X-ray polycrystalline diffraction (XRD)" is a conventional experimental method presently used for determining the structure of a crystal (i.e., crystal form). In an X-ray diffractometer, when the X-ray passes through a crystal, a serial of diffraction patterns are produced. The particular crystal form can be determined based on the diffraction patterns, because different diffracted rays and the strength thereof in the diffraction patterns represent particular atomic groups having particular structures.

The methods for determining the X-ray powder diffraction data of a crystal are known in the art. For example, a pattern can be obtained using a Cu radiation target on Bruker D8 Advanced X-ray powder diffractometer at a scan rate of 2° per min.

The lubiprostone crystal of the present invention has a special crystal morphosis, and has special characteristic peaks in the X-ray powder diffraction pattern. In particular, the lubiprostone crystal of the present invention has the main characteristic absorption peaks at the following 2θ reflection angles: 14.6±0.2°, 17.0±0.2°, and 19.6±0.2°. In a preferred embodiment, the pattern further comprises characteristic absorption peaks at the following 2θ reflection angles: 7.6±0.2°, 8.5±0.2°, 10.6±0.2°, 17.7±0.2°, 20.1±0.2° and 23.4±0.2°. More preferably, the X-ray powder diffraction pattern of the lubiprostone crystal is substantially the same as that shown in FIG. 1.

"Differential scanning calorimetry", also known as "differential calorimetric scanning analysis" (DSC), is a technique used to determine the relationship between the temperature and the energy difference of the substance to be tested and a reference substance. DSC patterns can be used to qualitatively identify a substance because the position, shape and number of the peaks in a DSC pattern are correlated with the property of the substance. Such a method is conventionally used in the art to determine various parameters, such as the phase transition temperature, glass transition temperature and reaction heat of a substance.

When a substance is in an amorphous form, the substance does not have a definite melting point in the procedure of heating. To the contrary, the lubiprostone crystal of the present invention has a definite melting point, i.e., the crystal can be transformed from a solid phase to a liquid phase within a relatively narrow temperature range in the procedure of heating.

The methods for carrying out DSC are known in the art. For example, a DSC scanning pattern of the crystal can be obtained by scanning from 25° C. to 300° C. on a DSC Q20 Differential scanning calorimeter at a ramp rate of 10° C. per min.

Figure 2:
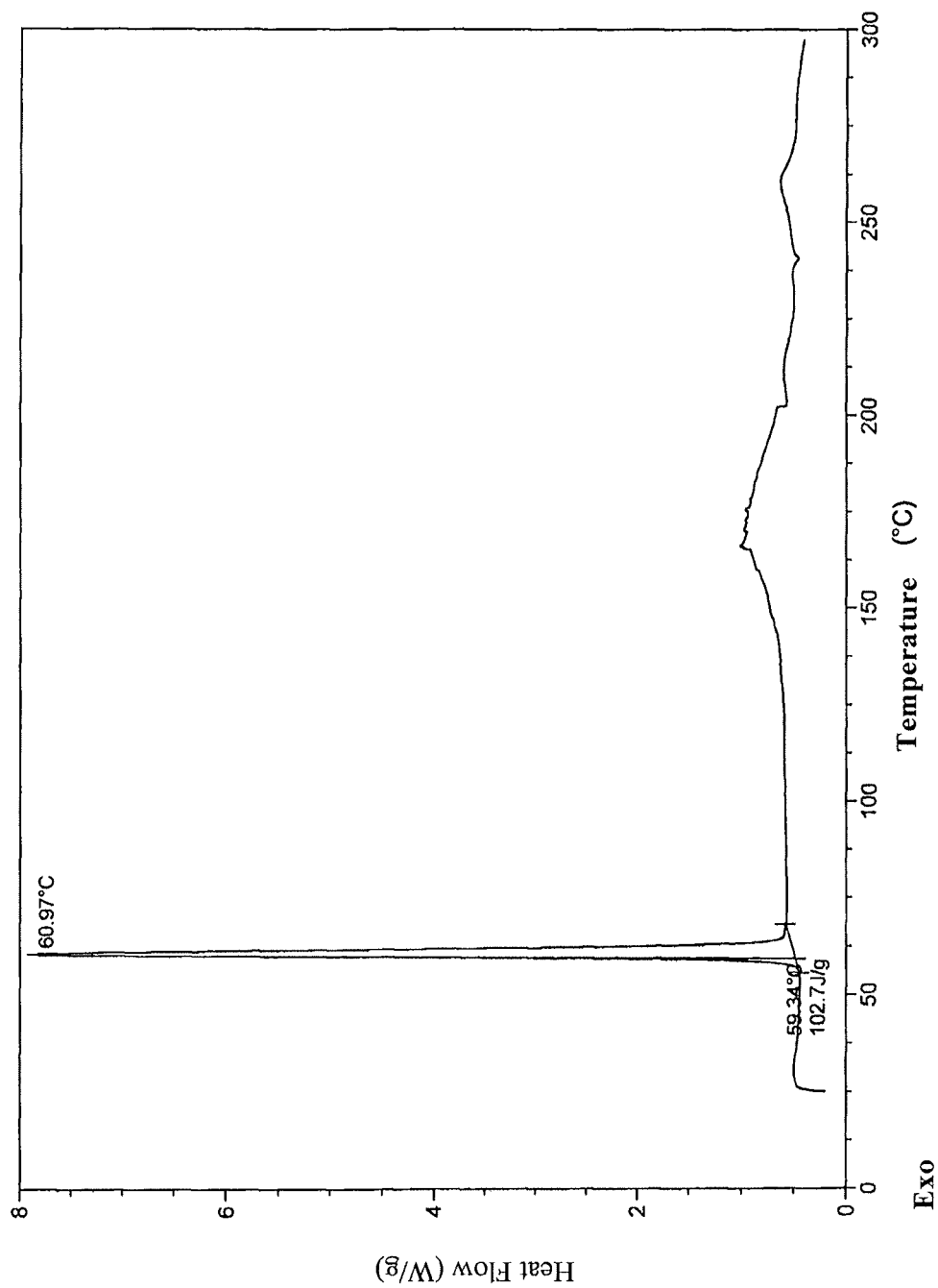
FIG. 2 is the differential scanning calorimetry (DSC) pattern of the lubiprostone crystal.

In one embodiment of the present invention, when measured by DSC, the lubiprostone crystal produced by the method of the present invention has a maximum peak value at about 61° C., preferably has substantially the same DSC pattern as that shown in FIG. 2, and more preferably has a maximum peak value at 60.97° C.

An infrared radiation (IR) pattern can also be used to determine the structure of a crystal, and the determining methods for IR are known in the art. For example, a PE Spectrum One B infrared radiator can be used to scan at 400~4000 cm$^{-1}$, and the sample can be prepared by pressing at a ratio of KBr:Sample=200:1. Preferably, the IR pattern for the lubiprostone crystal of the present invention is substantially the same as that shown in FIG. 3.

Use and Composition of the Lubiprostone Crystal

The lubiprostone crystal produced by the method of the present invention can be used as an API for providing or preparing a medicament for the treatment of gastrointestinal tract diseases (such as enhancing enterocinesia and relieving constipation symptoms) due to its high stability, easy-for-storage and use property, and high purity.

Consequently, the present invention further relates to a composition comprising the lubiprostone crystal of the present invention, wherein said composition comprises an effective amount of the lubiprostone crystal, and pharmaceutically acceptable carrier(s).

As used herein, the term "contain" or "comprise" includes the terms "include" or "be mainly consisted of" and "be consisted of". The term "an effective amount" refers to an amount that can produce the desired function or activity to humans and/or animals and can be accepted by said humans and/or animals.

As used herein, the term "pharmaceutically acceptable" means a substance which can be applied to humans and/or animals without undue side effects (such as toxicity, irritation, allergic response, and the like), i.e., a substance has reasonable benefit/risk ratio. The term "pharmaceutically acceptable carrier(s)" refers to carrier(s) used to deliver the therapeutic agents, and may comprise various excipients and diluents. This term may refer to pharmaceutical carrier(s) which are not themselves essential active components and without undue toxic after application. Suitable carriers are well known by the skilled in the art. The thorough discussion about pharmaceutically acceptable excipients can be found in Remington's Pharmaceutical Sciences (Mack Pub. Co., N.J. 1991).

Preferably, the "pharmaceutically acceptable carrier" is selected from the group consisting of: filler, disintegran, lubricant, glidant, effervescent, correctant, coating material, excipient, and/or delayed/controlled releasing agent. In a composition, the pharmaceutically acceptable carrier may comprise liquid(s), such as water, brine, glycerol, and ethanol. Moreover, the carrier may further comprise other adjuvant materials, such as filler, disintegran, lubricant, glidant, effervescent, wetting agent, emulsifier, correctant, and pH buffering substances and the like. Usually, these substances are formulated in an atoxic, inert and pharmaceutical acceptable aqueous vehicle medium, and the pH is usually about 5-8, and preferably 6-8.

In the pharmaceutical composition of the present invention, the lubiprostone crystal active component may take up 0.001~99.9 wt %, preferably 1~95 wt %, more preferably 5~90 wt %, and even more preferably 10~80 wt % of the total weight of the composition. The balance is pharmaceutically acceptable carrier(s) and other additives etc.

As used herein, the term "unit dosage form" refers to a dosage form comprising the composition of the present invention in a single dosage for the purpose of facilitating the administration. The term may comprise but not limited to various solid dosage forms (such as tablet), liquid dosage form, capsule, and delayed-releasing dosage form. In another preferred embodiment of the present invention, the composition is in a unit dosage form or a multiple dosage form, and wherein the amount of lubiprostone crystal is 0.01~2000 mg/dosage, preferably 0.1~1000 mg/dosage, and more preferably 1~500 mg/dosage.

Moreover, the pharmaceutical composition of the present invention may further comprise other active substance(s) which can be used to treat gastrointestinal tract diseases (such as enhancing enterocinesia and relieving constipation conditions). Said other active substance(s) can be, such as, proton pump inhibitors including but not limited to omeprazole, lansoprazole, or the combination thereof.

The composition of the present invention can be administrated via conventional routes comprising (but not limited to): oral administration, intramuscular injection, subcutaneous injection and so on, preferably oral administration. The form of the composition should match the administration route. Generally, the composition of the present invention may be administered in the amount of about 0.01-2000 mg/60 kg body weight per day, preferably about 0.05~1500 mg/60 kg body weight per day, more preferably 0.1~1000 mg/60 kg body weight per day, and most preferably 1~500 mg/60 kg body weight per day, based on the amount of the active substance(s).

In another preferred example of the present invention, the composition of the present invention may be administrated in 1~6 doses pre day, preferably 1~3 doses per day, and more preferable one dose per day. It should be appreciated that the effective dosage of lubiprostone crystal may be varied according to the severity of the conditions in a subject to be administrated or treated. The precise amount will depend upon the conditions of the individual (such as the body weight, age, health condition of the subject and the effect to be produced), and is within the scope of skilled clinicians or dietitians.

The composition of the present invention can be used alone, or in combination with other therapeutic agent(s) or adjuvants. In preferred embodiments of the present invention, the composition of the present invention may be applied in combination with an effective amount (such as 0.5-100 mg/60 kg body weight pre day, preferably 1-50 mg/60 kg body weight pre day) of other active substance(s), such as proton pump inhibitors including but not limited to omeprazole, lansoprazole, or the combination thereof.

When two or more medicaments are combined for the treatment, the effect is normally superior to that produced by applying these medicaments separately. Preferably, the therapeutic activity of the active component, the lubiprostone crystal of the present invention, will not be interfered by the medicament(s) or other agents applied in combination with said active component.

Of course, the lubiprostone crystal of the present invention may also be used to prepare a kit for the treatment of gastrointestinal tract diseases, wherein the kit comprises: the lubiprostone crystal of the present invention; other active substance(s) for the treatment of gastrointestinal tract diseases selected from proton pump inhibitors, such as omeprazole, lansoprazole, etc. The kit may optionally comprise: an instruction directing the customers or physicians to use said kit, container(s), excipient(s) and so on, which can be selected by the skilled in the art according to the particular need.

EXAMPLES

The invention is further illustrated in conjunction with the following examples. It is appreciated that these examples are only intended to illustrate the invention, but not to limit the scope of the invention. For the experimental methods in the following examples without detailed conditions, they are performed under routine conditions, or as instructed by the manufacturers. Unless otherwise specified, the percentages and parts are based on weight.

Unless otherwise specified, the technical and scientific terms used herein have the same meanings as those known by the skilled in the art. In addition, any method and material which similar to or identical with the contents disclosed herein can also be used in the present invention. The preferred methods and materials disclosed herein are only intended to illustrate the invention.

Example 1

The Preparation of Lubiprostone Crystal-1

A solution of 16,16-difluoro-13,14-dihydro-15-carbonyl-$PGE_2$ benzyl ester (8.44 g) in ethyl acetate (300 ml) was added into 5% Pd/C. The mixture was shaken under a hydrogen gas. Upon completion, the reaction mixture was filtrated, concentrated, and purified by silica gel column chromatography. The resultant was concentrated and dried to give an oily product (4.04 g), i.e., oily lubiprostone.

2.6 g oily lubiprostone was dissolved in 10 ml ethyl acetate at room temperature. To the solution, 200 ml n-hexane was added slowly and dropwise. The mixture was stirred at room temperature for 4 h to slowly precipitate a white solid and then stirred in ice-water bath for 1 h. 2.3 g white solid was obtained after sucking filtration and drying under reduced pressure. The XRD, DSC, and IR patterns of the product were shown in FIGS. 1-3.

Example 2

The Preparation of Lubiprostone Crystal-2

0.2 g oily lubiprostone (as prepared in Example 1) was dissolved in 0.5 ml acetone at room temperature. To the solution, 15 ml n-hexane was added slowly and dropwise. The mixture was stirred at room temperature for 4 h to slowly precipitate a white solid and then stirred in ice-water bath for 1 h. 0.16 g white solid was obtained after sucking filtration and drying under reduced pressure. The XRD, DSC, and IR patterns of the product were similar to those shown in FIGS. 1-3.

Example 3

The Preparation of Lubiprostone Crystal-3

0.2 g oily lubiprostone (as prepared in Example 1) was dissolved in 0.5 ml dichloromethane at room temperature. To the solution, 15 ml n-hexane was added slowly and dropwise. The mixture was stirred at room temperature for 4 h to slowly precipitate a white solid and then stirred in ice-water bath for 1 h. 0.17 g white solid was obtained after sucking filtration and drying under reduced pressure. The XRD, DSC, and IR patterns of the product were similar to those shown in FIGS. 1-3.

Example 4

The Preparation of Lubiprostone Crystal-4

0.2 g oily lubiprostone (as prepared in Example 1) was dissolved in 0.5 ml isopropanol at room temperature. To the solution, 15 ml n-hexane was added slowly and dropwise. The mixture was stirred at room temperature for 4 h to slowly precipitate a white solid and then stirred in ice-water bath for 1 h. 0.15 g white solid was obtained after sucking filtration and drying under reduced pressure. The XRD, DSC, and IR patterns of the product were similar to those shown in FIGS. 1-3.

Example 5

The Preparation of Lubiprostone Crystal-5

0.2 g oily lubiprostone (as prepared in Example 1) was dissolved in 0.5 ml acetone at room temperature. To the solution, 20 ml water was added slowly and dropwise. The mixture was stirred at room temperature for 4 h to slowly precipitate a white solid and then stirred in ice-water bath for 1 h. 0.14 g white solid was obtained after sucking filtration and drying under reduced pressure. The XRD, DSC, and IR patterns of the product were similar to those shown in FIGS. 1-3.

Example 6

The Preparation of Lubiprostone Crystal-6

0.2 g oily lubiprostone (as prepared in Example 1) was dissolved in 0.5 ml methol at room temperature. To the solution, 20 ml water was added slowly and dropwise. The mixture was stirred at room temperature for 4 h to slowly precipitate a white solid and then stirred in ice-water bath for 1 h. 0.13 g white solid was obtained after sucking filtration and drying under reduced pressure. The XRD, DSC, and IR patterns of the product were similar to those shown in FIGS. 1-3.

Example 7

Determination of the Characters of Lubiprostone Crystal

1. X-ray powder diffraction of lubiprostone crystal

Model of the Instrument: Bruker D8 Advanced

Method and parameters for detection: a Cu radiation target was used to obtain the pattern at a scan rate of 2° per minute.

Result of the Detection: the X-ray powder diffraction pattern of lubiprostone crystal was shown in FIG. 1, and the particular data were shown in Table 1:

TABLE 1

Corresponding data in the X-ray powder diffraction pattern of FIG. 1

| No. | Diffraction angle | d value | Relative intensity |
|---|---|---|---|
| 1 | 7.64 | 11.57 | 23.1 |
| 2 | 8.47 | 10.44 | 20.1 |
| 3 | 10.63 | 8.32 | 39.4 |
| 4 | 10.89 | 8.12 | 7.2 |
| 5 | 12.03 | 7.35 | 22.0 |
| 6 | 12.17 | 7.27 | 23.9 |
| 7 | 12.42 | 7.12 | 14.5 |
| 8 | 14.60 | 6.06 | 43.4 |
| 9 | 14.91 | 5.94 | 13.2 |
| 10 | 15.46 | 5.73 | 26.3 |
| 11 | 15.92 | 5.56 | 10.4 |
| 12 | 17.04 | 5.20 | 100.0 |
| 13 | 17.56 | 5.05 | 14.3 |
| 14 | 17.76 | 4.99 | 28.6 |
| 15 | 18.55 | 4.78 | 14.1 |
| 16 | 19.65 | 4.51 | 60.9 |
| 17 | 20.09 | 4.42 | 48.7 |
| 18 | 21.47 | 4.14 | 17.4 |
| 19 | 21.97 | 4.04 | 19.9 |
| 20 | 22.22 | 3.40 | 8.6 |
| 21 | 22.92 | 3.88 | 7.9 |
| 22 | 23.37 | 3.80 | 47.9 |
| 23 | 23.63 | 3.76 | 31.5 |
| 24 | 24.57 | 3.62 | 6.6 |
| 25 | 25.05 | 3.55 | 18.5 |
| 26 | 25.57 | 3.48 | 11.1 |
| 27 | 29.03 | 3.07 | 8.0 |
| 28 | 29.42 | 3.03 | 8.6 |
| 29 | 30.21 | 2.96 | 7.2 |
| 30 | 31.16 | 2.87 | 5.7 |
| 31 | 31.85 | 2.81 | 7.8 |
| 32 | 32.45 | 2.76 | 8.1 |
| 33 | 33.53 | 2.67 | 6.1 |
| 34 | 34.33 | 2.61 | 5.6 |
| 35 | 37.95 | 2.37 | 15.0 |
| 36 | 39.21 | 2.30 | 7.0 |
| 37 | 41.40 | 2.18 | 10.7 |
| 38 | 44.31 | 2.04 | 5.1 |

2. Differential Scanning Calorimetric Analysis of Lubiprostone Crystal

Instrument: DSC Q20 (TA)

Method and parameters for detection: the temperature was raised from 25° C. to 300° C. at a ramp rate of 10° C./min.

Result of the detection: the DSC pattern of lubiprostone was shown in FIG. 2 with an absorption peak at 60.97° C.

3. Infrared Scanning of Lubiprostone Crystal

Instrument: PE Spectrum One B

Method and parameters for detection: the sample was prepared by pressing at a ratio of KBr:Sample=200:1, and was scanned in the range of 400~4000 $cm^{-1}$.

Figure 3:
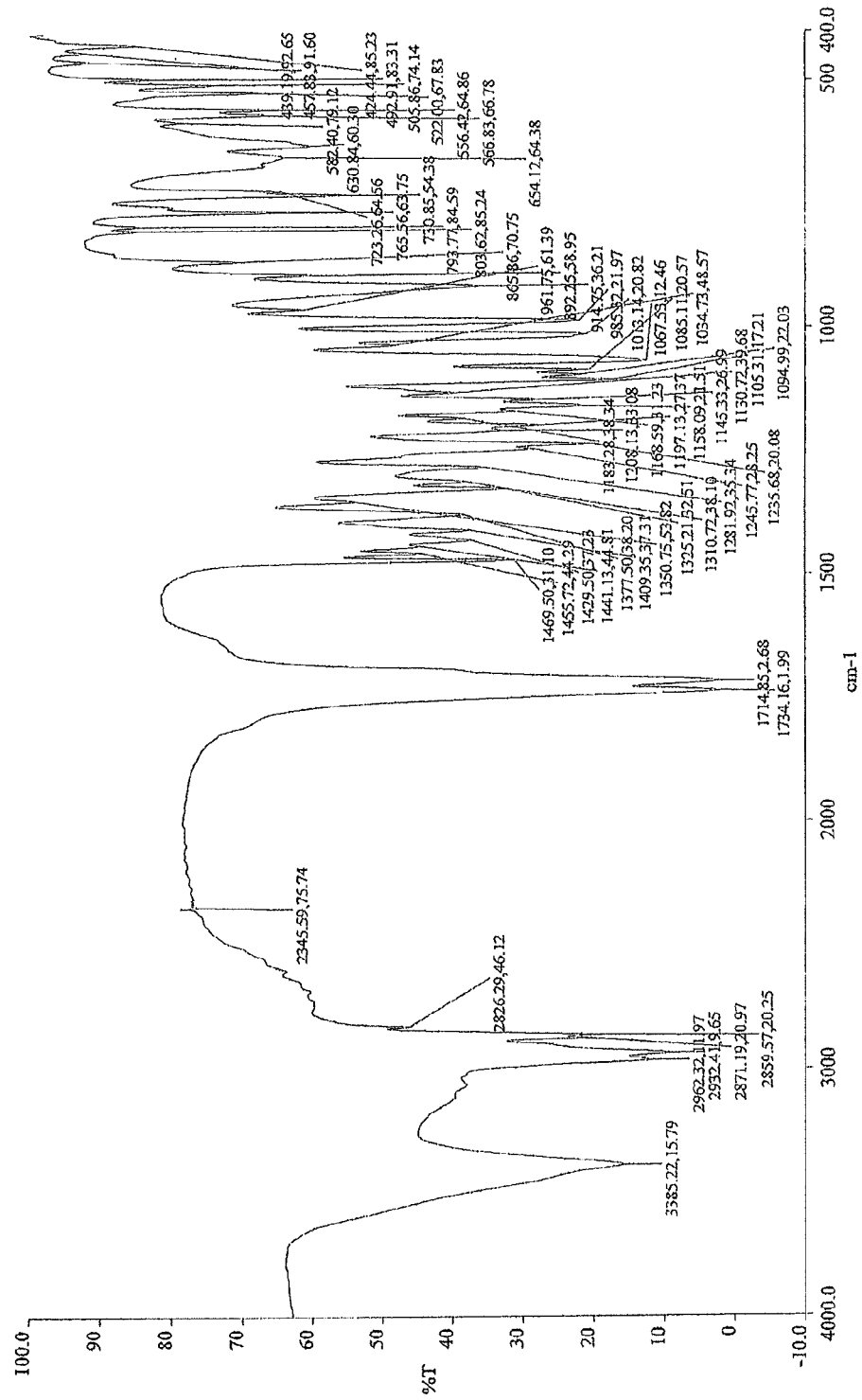
FIG. 3 is the infrared (IR) scanning image of the lubiprostone crystal.

Result of the Detection: the infrared scanning pattern was shown in FIG. 3.

Example 8

Comparison of the Stability

In the present Example, the stabilities of the oily lubiprostone (prepared according to Example 1) and the final products of Example 1 and Example 2 (crystal samples) were tested, and the results of the tests were compared.

Oily lubiprostone, the sample of Example 1, and the sample of Example 2 were separately sealed and placed at 40° C. for 7 days. After completion, the amount of the impurities was analyzed. The results were shown in Table 2.

TABLE 2

| Sample | Initial Product Amount | Product Amount (after 7 days at 40° C.) |
|---|---|---|
| Oily lubiprostone | 99.9% | 95.8% |
| Example 1 | 100.0% | 99.9% |
| Example 2 | 100.0% | 99.9% |

Based on the above data, it is clear that the lubiprostone crystal has excellent stability.

All literatures mentioned in the present application are incorporated by reference herein, as though individually incorporated by reference. Additionally, it should be understood that after reading the description above, many variations and modifications may be made by the skilled in the art, and these equivalents also fall within the scope as defined by the appended claims.

The invention claimed is:

1. A lubiprostone crystal, wherein the X-ray powder diffraction pattern of said crystal comprises characteristic peaks measured at the following 2θ reflection angles: 14.6±0.2°, 17.0±0.2° and 19.6±0.2°.

2. The lubiprostone crystal of claim 1, wherein the X-ray powder diffraction pattern of said crystal further comprises peaks measured at the following 2θ reflection angles: 7.6±0.2°, 8.5±0.2°, 10.6±0.2°, 17.7±0.2°, 20.1±0.2°, and 23.4±0.2°.

3. The lubiprostone crystal of claim 1, wherein, in the X-ray powder diffraction pattern of said crystal, the half peak width of the characteristic peaks at 2θ reflection angles is not more than 2°.

4. A method for preparing the lubiprostone crystal of claim 1, comprising:
dissolving lubiprostone in a solvent (i) to form a lubiprostone solution;
adding a solvent (ii) to the lubiprostone solution; and lowering the temperature of the lubiprostone solution containing the solvent (ii) to 10° to −50° to obtain said lubiprostone crystal, wherein said solvent (i) and said solvent (ii) are used as a pair (solvent (i) and solvent (ii)) selected from the group consisting of: ethyl acetate and n-hexane; acetone and n-hexane; dichloromethane and n-hexane; isopropanol and n-hexane; acetone and water; methanol and water; ethyl acetate and n-heptane; dichloromethane and cyclohexane; acetone and n-heptane; acetone and cyclohexane; dichloromethane and n-heptane; ethyl acetate and cyclohexane; isopropanol and n-heptane; isopropanol and cyclohexane; and isopropanol and water.

5. The method of claim 4, wherein the lubiprostone solution containing the solvent (ii) is stirred at room temperature before the step of lowering the temperature to 10° C. to −50° C.

6. A method of preparing a pharmaceutical composition for treating a gastrointestinal tract disease, comprising: mixing the lubiprostone crystal of claim 1 with a pharmaceutically acceptable carrier.

7. The method of claim 4, wherein the step of lowering the temperature of the lubiprostone solution containing the solvent (ii) comprises stirring the lubiprostone solution containing the solvent (ii) in an ice-water bath.

* * * * *